United States Patent
Lux et al.

(10) Patent No.: US 10,463,474 B2
(45) Date of Patent: Nov. 5, 2019

(54) MULTIFOCAL LENS

(71) Applicant: Rayner Intraocular Lenses Limited, West Sussex (GB)

(72) Inventors: Kirsten Lux, Mödling (AT); Nicole Plank, Forchtenstein (AT); Wolfgang Brezna, Wiener Neustadt (AT); Nikolaus Dragostinoff, Vienna (AT)

(73) Assignee: Rayner Intraocular Lenses Limited, West Sussex (GB)

( * ) Notice: Subject to any disclaimer, the term of this patent is extended or adjusted under 35 U.S.C. 154(b) by 0 days.

(21) Appl. No.: 15/765,078

(22) PCT Filed: Sep. 29, 2016

(86) PCT No.: PCT/EP2016/073361
§ 371 (c)(1),
(2) Date: Mar. 30, 2018

(87) PCT Pub. No.: WO2017/055510
PCT Pub. Date: Apr. 6, 2017

(65) Prior Publication Data
US 2018/0289469 A1 Oct. 11, 2018

(30) Foreign Application Priority Data
Oct. 2, 2015 (EP) .................................... 15188045

(51) Int. Cl.
*A61F 2/16* (2006.01)
*G02B 5/18* (2006.01)
(Continued)

(52) U.S. Cl.
CPC .......... *A61F 2/1618* (2013.01); *A61F 2/1654* (2013.01); *G02B 3/08* (2013.01);
(Continued)

(58) Field of Classification Search
CPC ................. A61F 2/1613; A61F 2/1654; G02C 7/041–7/045; G02C 7/06–7/068; G02C 2202/20; G02B 3/08; G02B 5/1876
(Continued)

(56) References Cited

U.S. PATENT DOCUMENTS

| 5,344,447 A | 9/1994 | Swanson |
| 5,760,871 A | 6/1998 | Kosoburd et al. |

(Continued)

FOREIGN PATENT DOCUMENTS

| CA | 2175632 A1 | 11/1996 |
| CA | 2741158 A1 | 4/2010 |

(Continued)

*Primary Examiner* — Zachary W Wilkes
(74) *Attorney, Agent, or Firm* — Hodgson Russ LLP

(57) ABSTRACT

The invention relates to a multifocal lens (1) with a refractive focus ($F_r$) and with a diffractive structure (5) which, in the radial direction (r) of the lens (1), plotted across the squared radius ($r^2$), has a periodic profile (6, 7, 8, 9), wherein the profile (6, 7, 8, 9) per period has four adjoining portions (6, 7, 8, 9) which are not differentiable at their connection sites (10, 11, 12, 13), wherein a first portion (9) has a monotonically falling function and the three further portions (6, 7, 8) have a monotonically rising function or vice versa, and wherein the further portion (7), which does not adjoin the first portion (9), has a greater pitch than the other further portions (6, 8).

7 Claims, 3 Drawing Sheets

(51) Int. Cl.
  *G02B 3/08* (2006.01)
  *G02C 7/04* (2006.01)
(52) U.S. Cl.
  CPC ........... *G02B 5/1876* (2013.01); *G02C 7/042* (2013.01); *G02C 7/044* (2013.01); *G02C 2202/20* (2013.01)
(58) Field of Classification Search
  USPC ............ 351/159.11, 159.15, 159.26, 159.35; 359/741–743, 565
  See application file for complete search history.

(56) References Cited

U.S. PATENT DOCUMENTS

| | | | | |
|---|---|---|---|---|
| 5,982,543 | A * | 11/1999 | Fiala | G02B 5/1895 351/159.01 |
| 6,560,019 | B2 * | 5/2003 | Nakai | G02B 5/1866 359/566 |
| 8,995,058 | B2 * | 3/2015 | Okada | G02B 5/1814 359/574 |
| 9,101,466 | B2 | 8/2015 | Hong | |
| 9,335,564 | B2 * | 5/2016 | Choi | G02C 7/06 |
| 2006/0116764 | A1 | 6/2006 | Simpson | |
| 2009/0268155 | A1 | 10/2009 | Weeber | |
| 2010/0066973 | A1 | 3/2010 | Portney | |
| 2011/0234974 | A1 | 9/2011 | Lawu | |
| 2014/0347624 | A1 | 11/2014 | Ando et al. | |
| 2018/0275428 | A1 * | 9/2018 | Ando | G02C 7/04 |

FOREIGN PATENT DOCUMENTS

| | | |
|---|---|---|
| CA | 2880365 A1 | 11/2015 |
| CN | 102256567 A | 11/2011 |
| DE | 202009018881 U1 | 2/2014 |
| EP | 2503962 B1 | 7/2013 |
| JP | H07198909 A | 8/1995 |
| JP | 2005292860 A | 10/2005 |
| JP | 2013049272 A | 3/2013 |
| JP | 2013517822 A | 5/2013 |
| RU | 2538935 C2 | 1/2015 |
| WO | 2010079528 A1 | 7/2010 |

\* cited by examiner

MULTIFOCAL LENS

CROSS-REFERENCE TO RELATED APPLICATIONS

This application is a National Phase of PCT/EP2016/073361, filed Sep. 29, 2016, which claims priority to European Patent Application No. 15188045.7, filed Oct. 2, 2015, the disclosure of which is incorporated herein by reference.

Field of the Disclosure

The present invention relates to a multifocal lens with a refractive focal point and a diffractive structure, the structure having a periodic profile in the radial direction of the lens plotted over the squared radius, and the profile having four mutually adjacent portions per period which cannot be differentiated at their junctions.

BACKGROUND OF THE DISCLOSURE

Multifocal intraocular or contact lenses, i.e. lenses with a plurality of focal points, which may for example be used for near and distance vision (bifocal) or near, intermediate and distance vision (trifocal), have been known for several decades and use a very wide range of diffractive structures on a refractive basic lens, in order to provide one or more diffractive focal points in addition to the refractive focal point.

According to documents DE 20 2009 018 881 U1 and EP 2 503 962 B1, to produce two diffractive focal points lenses with diffractive structures are used, the profile of which per period has four alternately monotonically rising and monotonically falling portions, i.e. two acute-angled maxima per period. The applicant has recognised that incorporating such structures into the lens not only leads to a plurality of profile peaks which are difficult to manufacture, but also to suboptimal distribution or light yield of the light intensities in the focal points produced.

SUMMARY OF THE DISCLOSURE

The object of the invention is to provide an improved lens which overcomes the disadvantages of the prior art. According to the invention, the object is achieved with a lens of the above-stated type in which a first portion of the profile falls monotonically and the three further portions rise monotonically, or a first portion rises monotonically and the three further portions fall monotonically, and wherein the further portion which does not adjoin said first portion has a steeper gradient than the other two further portions.

With the structure according to the invention, a lens is provided whose focal points usable for near, intermediate and distance vision have a higher intensity component than is known in the prior art. For more precise consideration of the problem, "positive" order diffractive focal points will hereinafter be defined as those which are located between the lens and its refractive focal point, and "negative" order diffractive focal points as those which are located on the side of the refractive focal point remote from the lens.

If the refractive focal point is used for distance vision, for example, the first positive order focal point of the diffractive structure corresponds to a distance for intermediate vision and the second positive order focal point of the diffractive structure to a distance for near vision. The respective negative focal points of the diffractive structure will in this case form an image only behind the lens user's retina, for which reason they are not useful to the user and contribute to an impairment of image quality.

In the case of the lens according to the invention, in contrast, intensity components of the (originally) negative orders are imaged onto the positive orders used or onto the zeroth (refractive) order, resulting in a more intensely coloured, higher contrast image compared to the prior art, since the useful focal points comprise higher intensity components.

The same advantages are obtained if, for example in an alternative embodiment, the refractive focal point is used for near vision, and the first negative order focal point of the diffractive structure corresponds to a distance for intermediate vision and the second negative order focal point of the diffractive structure corresponds to a distance for distance vision. In this embodiment, the positive orders of the diffractive structures are of little use, since they are located in front of the near vision focal point, and the third negative order orders are of no use at all, since they are only focused behind the retina. According to the invention, intensity components of the positive orders are here imaged onto the zeroth (refractive) negative first and negative second order, again resulting in a higher light yield in the useful focal points and thus a more intensely coloured, higher contrast image compared to the prior art.

In each embodiment, the lens according to the invention lens additionally has the significant advantage that the diffractive structure of the lens comprises just one maximum per period and nonetheless produces two diffractive focal points. Production of the diffractive structure on the lens may thus proceed far more simply and with less waste, since the angle of the maximum is larger and moreover only occurs once per period, i.e. only half as often as with the diffractive structures according to the prior art, which produce two diffractive focal points. Higher lens accuracy may be achieved in particular at the periphery of the lens, at which the period lengths may be very small, due to the more precise manufacture made possible thereby, leading in turn to more precise, more controlled light distribution.

The refractive focal point of the lens may, as discussed, be used either for near vision or distance vision. If the refractive focal point is used for distance vision, the preferred embodiment is the one in which the first portion falls monotonically and the three further portions rise monotonically. Alternatively, the refractive focal point may be used for near vision, wherein the first portion then preferably rises monotonically and the three further portions fall monotonically.

The portions, plotted over the squared radius, are preferably linear, i.e. they result in quadratically rising or falling flanks on the lens. This allows a simple calculation of the intensity profile of the lens. Alternatively, the portions may also comprise individual profiles, in order to adapt the intensity distribution of the lens.

In one preferred embodiment, the stated first portion is substantially vertical. Irrespective thereof, the further portion which does not adjoin the first portion may also be substantially vertical. These two measures result in an extremely simple profile pattern, since then only the gradient of two portions remains to be determined. This also simplifies manufacture of the lens, because a vertical portion, plotted over the squared radius, also results in a vertical flank on the lens.

To simplify calculation of the profile and consequently also manufacture of the lens, the two further portions which each adjoin the first portion, plotted over the squared radius, may have substantially the same gradient.

In one practical embodiment, two further portions which each adjoin the first portion, plotted over the squared radius, have a gradient of 1 µm/mm² to 10 µm/mm². Furthermore, the period of the profile, plotted over the squared radius, preferably amounts to 0.5 mm² to 1 mm² and the profile depth to 2 µm to 10 µm. This yields a lens whose focal points for near and intermediate vision lie at distances desired by users.

The invention is explained in greater detail below on the basis of exemplary embodiments shown in the appended drawings, in which:

DETAILED DESCRIPTION OF THE DISCLOSURE

Figure 1:
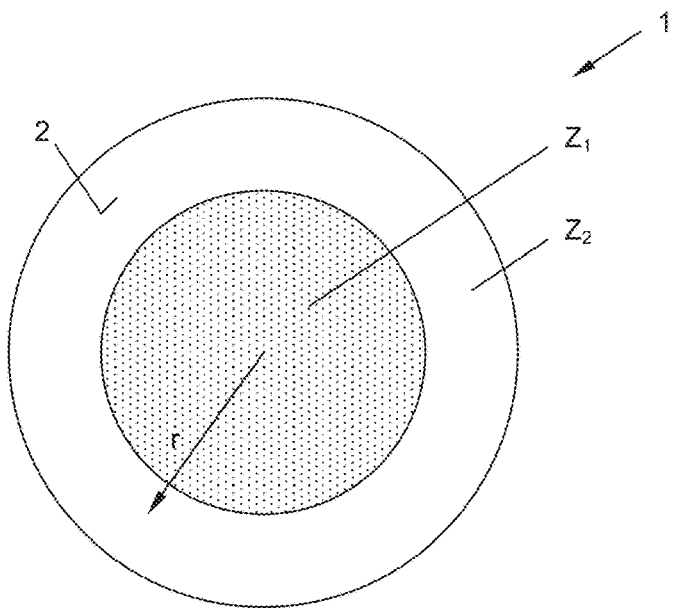
FIG. 1 is a schematic plan view of the lens according to the invention.
Figure 2:
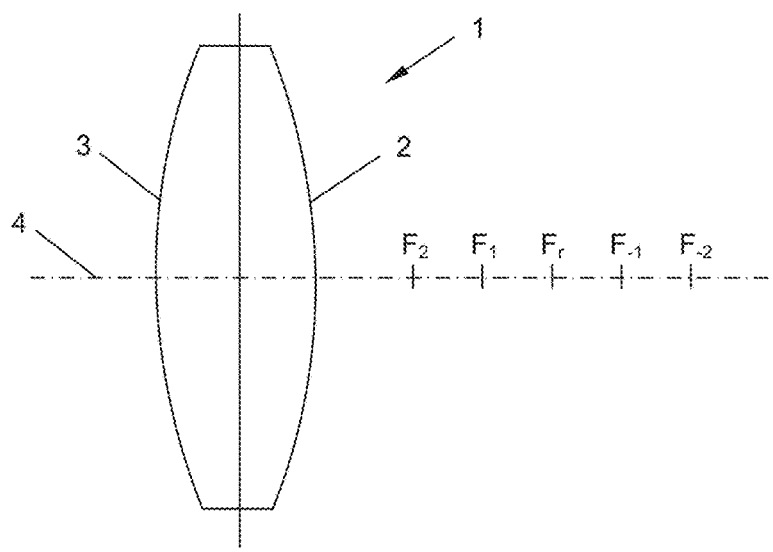
FIG. 2 is a schematic side view of the lens of FIG. 1.

FIGS. 1 and 2 show a lens 1 with a front face 2, a back face 3 and an optical axis 4. The lens 1 has a central zone $Z_1$ and an annular zone $Z_2$, which are explained in further detail below. The described lens 1 is used in particular as an intraocular lens or contact lens, but may also be used in optical equipment.

Figure 3:
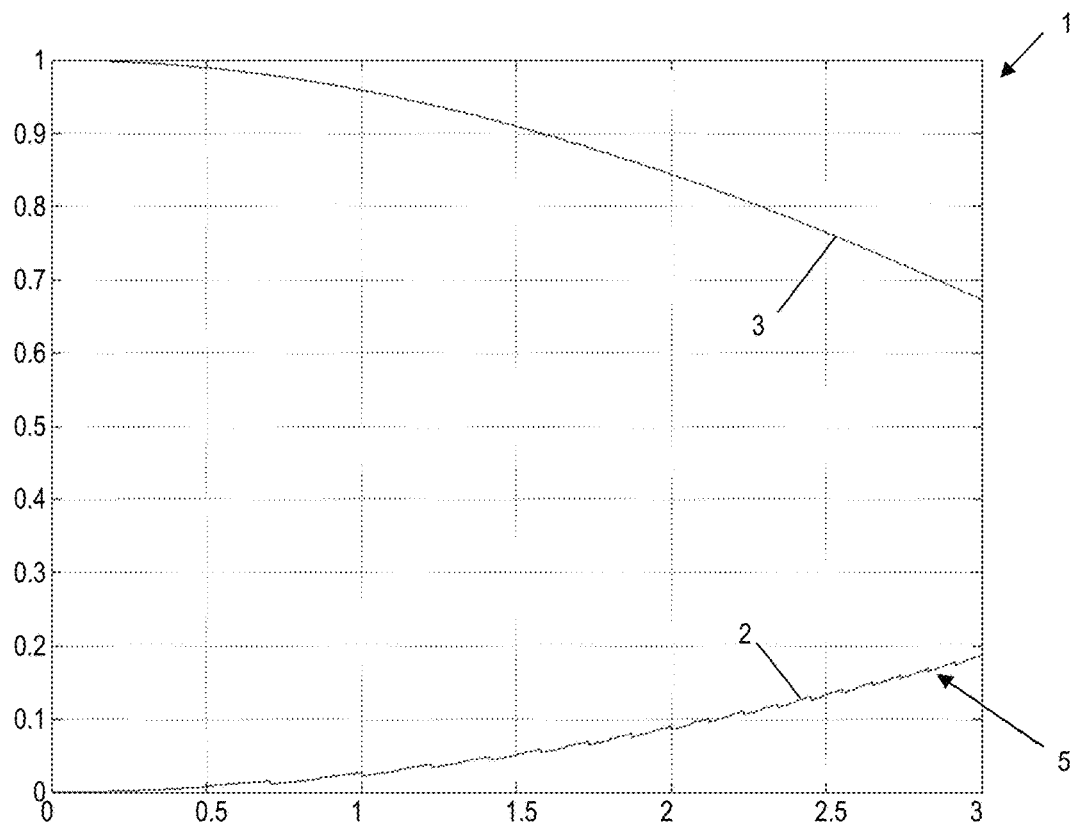
FIG. 3 shows an enlarged half section of the lens of FIG. 1.

The lens 1 has a refractive focal point $F_r$ located on the optical axis 4, which focal point may be used, as described below, for distance or near vision and is also described hereinafter as a zeroth order focal point. A diffractive structure 5 is incorporated into the back or front 2, 3 of the lens 1, see FIGS. 3 and 4, in order to adapt the lens 1 both to near and to intermediate and distance vision.

The diffractive structure 5 generates a plurality of further focal points $F_i$ (i = . . . , −2, −1, 1, 2 etc.) located on the optical axis 4 which are distributed symmetrically around the refractive focal point $F_r$, wherein the refractive focal point $F_r$ is provided by the shape of the lens 1, irrespective of the plotted diffractive structure 5. The diffractive focal points $F_1$, $F_2$ are described as positive first or second order focal points respectively of the diffractive structure 5 and lie on the optical axis 4 between the lens 1 and the refractive focal point $F_r$. The diffractive focal points $F_{-1}$, $F_{-2}$ are described as negative first or second order focal points respectively of the diffractive structure 5 and lie on the side of the refractive focal point $F_r$ remote from the lens 1.

Although the (position) distribution of the focal points $F_i$ is symmetrical around the refractive focal point $F_r$, the intensity distribution assigned to the respective focal points $F_i$ is not intended to be symmetrical. For instance, in the case of a trifocal lens in particular three maximum intensities are intended to form, namely for distance, intermediate and near vision. This is achieved by forming the diffractive structure 5 according to FIG. 4.

Figure 4:
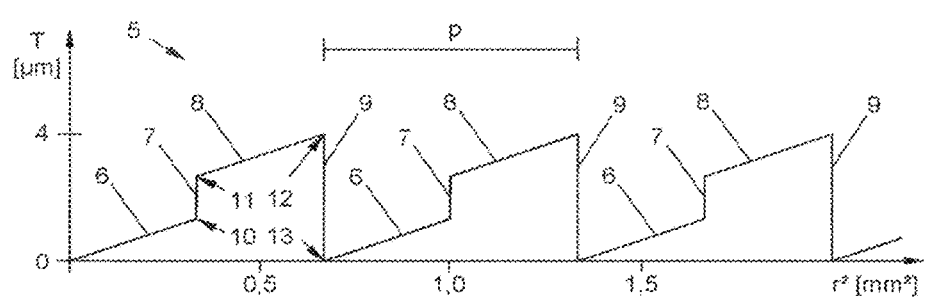
FIG. 4 shows the profile of the diffractive structure of the lens of FIGS. 1-3, plotted over the squared radius of the lens.

According to FIG. 4 (x-axis: squared radius r² [mm]; y-axis: profile depth T [µm]) the diffractive structure 5 comprises a periodic profile in the radial direction r of the lens 1, plotted over the squared radius r², which has four mutually adjacent portions 6, 7, 8, 9 per period p which cannot be differentiated at their junctions 10, 11, 12, 13. The phrase "plotted over the squared radius" means, with regard to periodicity, that the period intervals p diminish on the lens 1.

In an intraocular or contact lens, for example, the period p may lie in the range from 0.5 mm² to 1 mm² and the profile depth T in the range from 2 µm to 10 µm.

In the embodiment of FIG. 4, an arbitrary "first" portion of the profile 5, here the portion 9, falls monotonically and the three further portions 6, 7, 8 of the profile rise monotonically. The expression "first" used herein does not relate to the order of the portions 6-9, but rather serves merely to draw a distinction from three "further" portions. The order of the portions 6-9 within a period p may thus be freely selected or defined, whereby for example each of the portions 6, 7, 8, 9 may be selected as the "starting" portion and/or the "first" portion 9 does not necessarily lie at the start of the period p.

Figure 5:
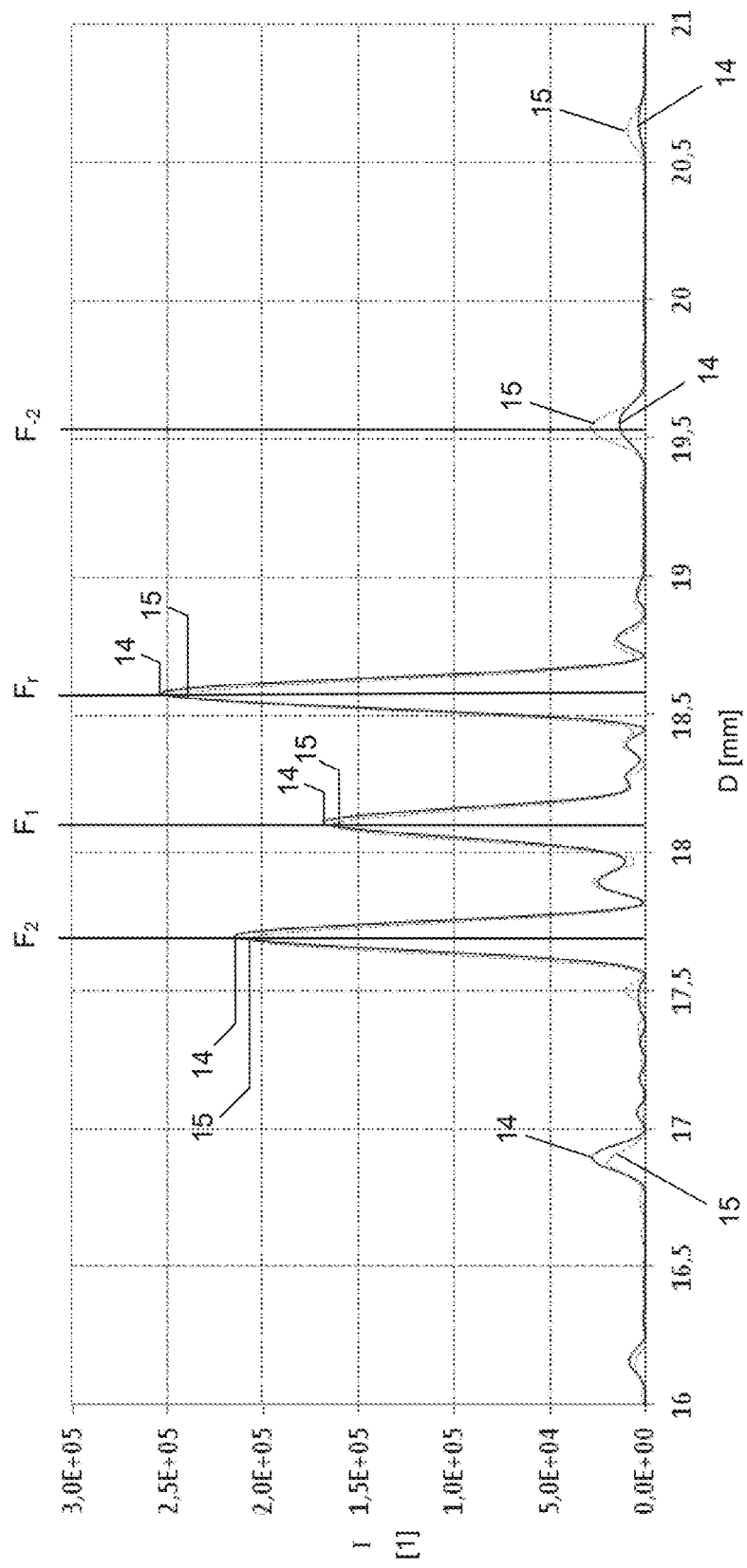
FIG. 5 shows a comparison of the intensity distribution of the lens according to the invention with that of a lens according to the prior art.

In the embodiment shown in FIG. 4, the refractive focal point $F_r$ is designed for distance vision and the three monotonically rising further portions 6, 7, 8 and the monotonically falling first portion 9 result in two positive order diffractive focal points $F_1$, $F_2$ for near and intermediate vision (see FIG. 5). Alternatively, the refractive focal point $F_r$ may for example also be designed for near vision, to which end three monotonically falling further portions 6, 7, 8 and one monotonically rising first portion 9 are then used, resulting in two negative order diffractive focal points $F_{-1}$, $F_{-2}$ for intermediate and distance vision (not shown).

The further portion which does not adjoin the first portion 9, i.e. in FIG. 4 the middle further portion 7, has a steeper gradient than the other two further portions 6, 8. The term "gradient" is defined herein as the total gradient covered by a portion 6, 7, 8, 9, i.e. as the gradient between the starting point of a portion 6, 7, 8 or 9 and the end point of the same portion 6, 7, 8 or 9.

The portions 6-9, plotted over the squared radius r², may be linear, whereby a monotonically rising portion 6, 7, 8 on the lens 1 gives rise to a flank rising quadratically with r.

According to FIG. 4, moreover, the first portion 9 and the further portion which does not adjoin the first portion 9, i.e. here the middle further portion 7, are substantially vertical, i.e. they have a gradient of +/−∞.

Alternatively, these two portions 7, 9 may also each mutually independently have a finite gradient (not shown).

The two further portions 6, 8 which each adjoin the first portion 9 have substantially the same gradient, plotted over the squared radius r². In the case of an intraocular or contact lens, the gradient may for example lie in the range from 1 µm/mm² to 10 µm/mm². The two portions 6, 8 may also comprise mutually different gradients (not shown).

The diffractive structure 5 may either be applied to the entire surface of one side 2, 3 of the lens 1 or merely in a central region $Z_1$ or an annular region $Z_2$ of the lens 1, as shown in FIG. 1. Alternatively or in addition, the structure 5 may be apodised. This means that the profile depth T of the structure 5 decreases as the lens radius r increases.

To produce the lens 1, the diffractive structure 5 may for example be incorporated directly into a lens blank, for example by turning on a lathe. The lens blank could however also merely be a processable starting material for a 3D printer, with incorporation of the structure into the lens blank then proceeding by 3D printing of the starting material to yield the multifocal lens 1.

Alternatively, the diffractive structure 5 could initially also be incorporated as a negative into a moulded blank, for example again by means of a lathe or a 3D printer Then, a lens material is brought into contact with the moulded blank in order in this way to produce the multifocal lens 1. The lens material may for example already have been prefabricated into a lens blank, into which the structure 5 is pressed or impressed by means of the moulded blank acting as a "punch". Alternatively, the lens material may be present in a liquid or viscous state and be cast onto the moulded blank, for example in a mould. The lens material is then hardened, for example by the input of light or heat.

FIG. 5 shows a comparison of the intensity profile 14 (shown by a solid line) of the lens 1 presented here with the intensity profile 15 (shown by a broken line) of a lens according to the prior art (x-axis: distance D from the lens [mm]; y-axis: relative intensity I [1]).

The lens 1 used for this comparison with the diffractive structure 5 presented herein had a period p, plotted over the squared radius $r^2$, of 0.65 mm$^2$, wherein the profile depth T was 4.4 μm. The two further portions 6, 8 which in each case adjoined the first portion 9 had, plotted over the squared radius $r^2$, a gradient of 4.3 μm/mm$^2$.

In contrast, the comparison line relating to the prior art had a periodic profile which within one period had four portions which successively rose, fell, rose and fell monotonically.

As is clear from the diagram of FIG. 5, the result is a similar intensity distribution profile in the region of the refractive focal point $F_r$. It is however readily apparent from FIG. 5 that the lens 1 according to the prior art had greater intensity values in the region of the second negative focal point $F_{-2}$ of the diffractive structure 5. In contrast, in the case of the lens 1 presented here, non-usable, negative order intensities are shifted into usable positive orders, as is apparent from the markedly increased intensities of the profile 10 at the focal points $F_1$ and $F_2$, and the markedly reduced intensity of the profile 14 at the focal point $F_{-2}$. A more intensely coloured and higher contrast image is thus obtained for the user of the described lens 1 than with lenses according to the prior art The invention is accordingly not limited to the embodiments shown but rather comprises all variants, modifications and combinations thereof which fall within the scope of the appended claims.

The invention claimed is:

1. A multifocal lens with a refractive focal point ($F_r$) and a diffractive structure, the structure having a periodic profile in the radial direction (r) of the lens plotted over the squared radius ($r^2$), and
   the profile having four mutually adjacent portions per period which cannot be differentiated at their junctions,
   the four portions including a first portion, a second portion, a third portion, and a fourth portion, wherein the first portion is adjacent to the fourth portion and the second portion, and the third portion is adjacent to the second portion and the fourth portion,
   wherein the first portion falls monotonically and the second portion, the third portion, and the fourth portion each rise monotonically, or a first portion rises monotonically and the second portion, the third portion, and the fourth portion each fall monotonically, and
   wherein the third portion has a steeper gradient than the second portion and the fourth portion, and wherein the fourth portion and the second portion have, plotted over the squared radius ($r^2$), a gradient of 1 μm/mm$^2$ to 10 μm/mm$^2$.

2. The multifocal lens according to claim 1, wherein the first portion, the second portion, the third portion, and the fourth portion each are linear when plotted over the squared radius ($r^2$).

3. The multifocal lens according to claim 1, wherein the first portion is substantially vertical.

4. The multifocal lens according to claim 1, wherein the third portion is substantially vertical.

5. The multifocal lens according to claim 1, wherein the second portion and the fourth portion have substantially the same gradient.

6. The multifocal lens according to claim 1, wherein the period (p) of the profile, plotted over the squared radius, amounts to 0.5 mm$^2$ to 1 mm$^2$ and the profile depth (T) to 2 μm to 10 μm.

7. The multifocal lens according to claim 1, wherein the multifocal lens is an intraocular lens or contact lens.

* * * * *